(12) United States Patent
Williamson et al.

(10) Patent No.: US 7,942,845 B2
(45) Date of Patent: May 17, 2011

(54) NEEDLE-FREE INJECTOR AND PROCESS FOR PROVIDING SERIAL INJECTIONS

(75) Inventors: Daniel E. Williamson, Sherwood, OR (US); Ryan R. Beylund, Milwaukie, OR (US); Keith K. Daellenbach, Portland, OR (US)

(73) Assignee: Bioject, Inc., Tualatin, OR (US)

( * ) Notice: Subject to any disclaimer, the term of this patent is extended or adjusted under 35 U.S.C. 154(b) by 777 days.

(21) Appl. No.: 11/765,245

(22) Filed: Jun. 19, 2007

(65) Prior Publication Data

US 2008/0071211 A1   Mar. 20, 2008

Related U.S. Application Data

(60) Provisional application No. 60/826,204, filed on Sep. 19, 2006.

(51) Int. Cl.
*A61M 5/30* (2006.01)
(52) U.S. Cl. .............. 604/68; 604/70; 604/71
(58) Field of Classification Search .......... 604/68–71
See application file for complete search history.

(56) References Cited

U.S. PATENT DOCUMENTS

| | | | |
|---|---|---|---|
| 3,202,151 A * | 8/1965 | Kath | ........ 604/71 |
| 4,596,556 A | 6/1986 | Morrow et al. | |
| 4,790,824 A | 12/1988 | Morrow et al. | |
| 4,940,460 A | 7/1990 | Casey et al. | |
| 4,941,880 A | 7/1990 | Burns | |
| 5,064,413 A | 11/1991 | McKinnon et al. | |
| 5,312,335 A | 5/1994 | McKinnon et al. | |
| 5,312,577 A | 5/1994 | Peterson et al. | |
| 5,383,851 A | 1/1995 | McKinnon, Jr. et al. | |
| 5,399,163 A | 3/1995 | Peterson et al. | |
| 5,503,627 A | 4/1996 | McKinnon et al. | |
| 5,505,697 A | 4/1996 | McKinnon, Jr. et al. | |
| 5,520,639 A | 5/1996 | Peterson et al. | |
| 5,716,009 A | 2/1998 | Ogihara et al. | |
| 5,746,714 A | 5/1998 | Salo et al. | |
| 5,782,802 A | 7/1998 | Landau | |
| 5,893,397 A | 4/1999 | Peterson et al. | |
| 5,993,412 A | 11/1999 | Deily et al. | |
| 6,096,002 A | 8/2000 | Landau | |

(Continued)

FOREIGN PATENT DOCUMENTS

EP    0427457    5/1991

(Continued)

OTHER PUBLICATIONS

International Search Report for Application No. PCT/US2007/020254.

(Continued)

*Primary Examiner* — Nicholas D Lucchesi
*Assistant Examiner* — Ian K Holloway
(74) *Attorney, Agent, or Firm* — Schwabe, Williamson & Wyatt, P.C.

(57) ABSTRACT

Needle-free injection devices having a drive assembly to provide an operative force to effect an injection and a dosing assembly to prepare the device for a subsequent injection. In some embodiments, the dosing assembly is configured to transfer injectate from an injectate source to the injectate assembly. In some embodiments, a portion of energy available to the drive assembly urges the injectate towards the injectate assembly. In some embodiments, the device includes a nozzle assembly having one or more ports.

10 Claims, 5 Drawing Sheets

U.S. PATENT DOCUMENTS

| | | | |
|---|---|---|---|
| 6,132,395 | A | 10/2000 | Landau |
| 6,216,493 | B1 | 4/2001 | Weston et al. |
| 6,264,629 | B1 | 7/2001 | Landau |
| 6,295,986 | B1 | 10/2001 | Patel et al. |
| 6,319,224 | B1 | 11/2001 | Stout et al. |
| 6,383,168 | B1 | 5/2002 | Landau et al. |
| 6,415,631 | B1 | 7/2002 | Weston et al. |
| 6,471,669 | B2 | 10/2002 | Landau |
| 6,572,581 | B1 | 6/2003 | Landau |
| 6,585,685 | B2 | 7/2003 | Staylor et al. |
| 6,607,510 | B2 | 8/2003 | Landau |
| 6,623,446 | B1 | 9/2003 | Navelier et al. |
| 6,641,554 | B2 | 11/2003 | Landau |
| 6,645,170 | B2 | 11/2003 | Landau |
| 6,676,630 | B2 | 1/2004 | Landau et al. |
| 6,689,093 | B2 | 2/2004 | Landau |
| 6,709,427 | B1 | 3/2004 | Nash et al. |
| 6,716,190 | B1 | 4/2004 | Glines et al. |
| 6,752,780 | B2 | 6/2004 | Stout et al. |
| 6,752,781 | B2 * | 6/2004 | Landau et al. .................. 604/70 |
| 6,783,509 | B1 | 8/2004 | Landau et al. |
| 6,935,384 | B2 | 8/2005 | Landau et al. |
| 6,942,645 | B2 | 9/2005 | Alexandre et al. |
| 6,979,310 | B2 | 12/2005 | Navelier et al. |
| 6,981,961 | B1 | 1/2006 | Navelier et al. |
| 7,056,300 | B2 | 6/2006 | Alexandre et al. |
| 7,156,823 | B2 | 1/2007 | Landau et al. |
| 2004/0111054 | A1 * | 6/2004 | Landau et al. .................. 604/68 |
| 2004/0210188 | A1 * | 10/2004 | Glines et al. .................. 604/68 |
| 2006/0189927 | A1 | 8/2006 | Alexandre et al. |

FOREIGN PATENT DOCUMENTS

| | | |
|---|---|---|
| WO | WO0072908 | 12/2000 |
| WO | 0137906 | 5/2001 |

OTHER PUBLICATIONS

Written Opinion of the International Searching Authority for Application No. PCT/US2007/020254.

Additional Disclosure Regarding the Devices of U.S. Patent Application Publication No. US 2004/0111054 A1, prepared Feb. 2010.

* cited by examiner

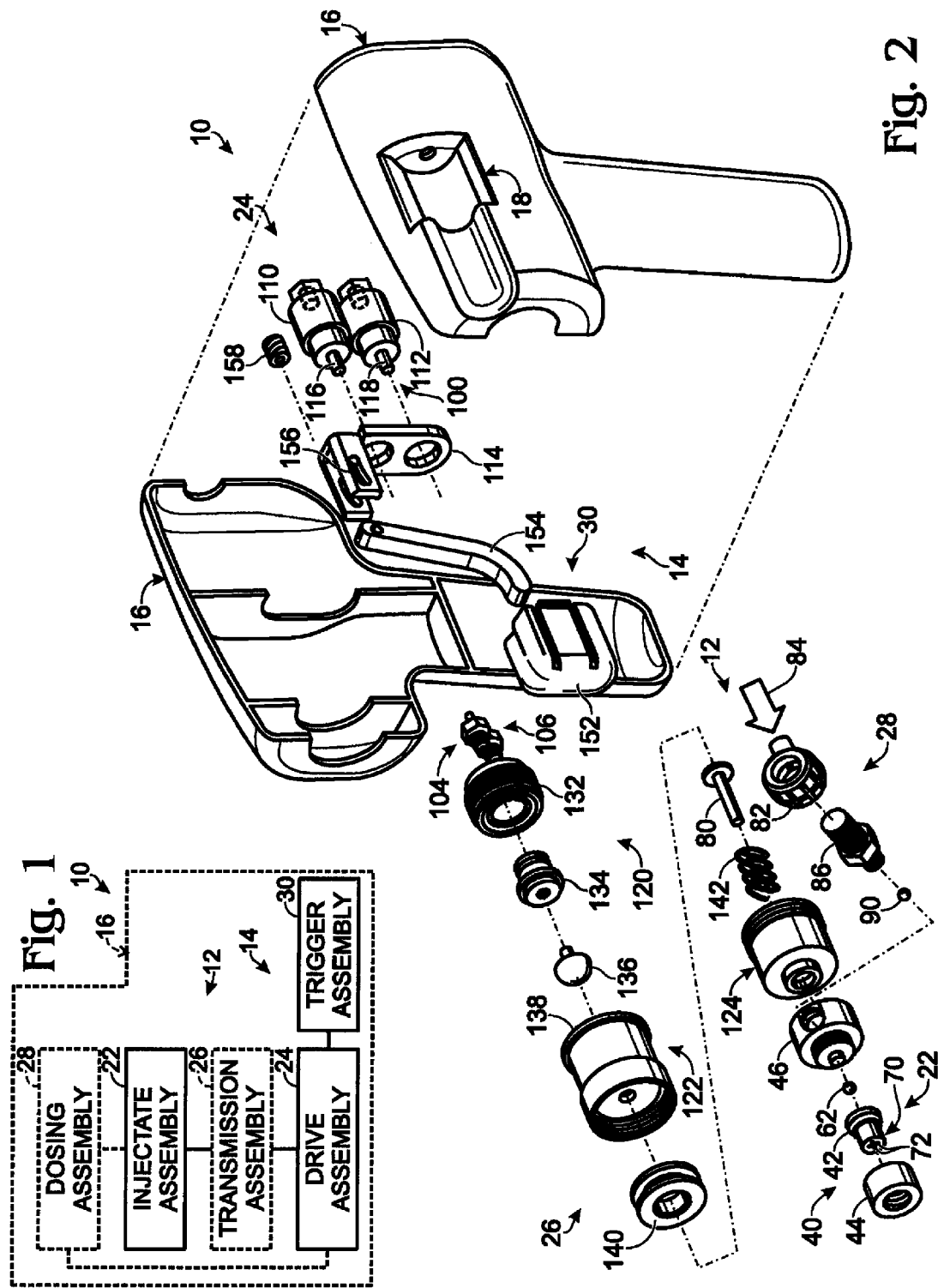

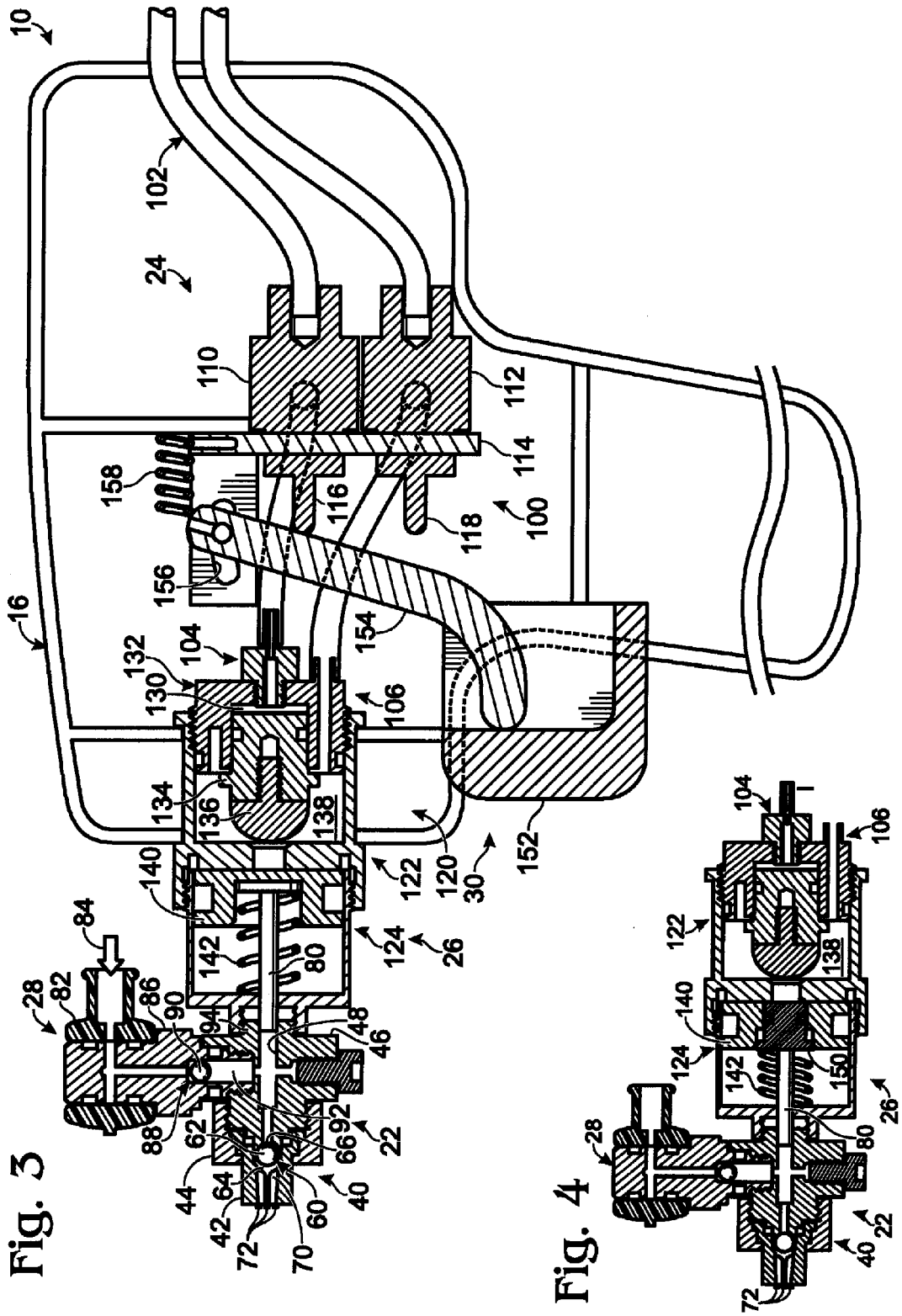

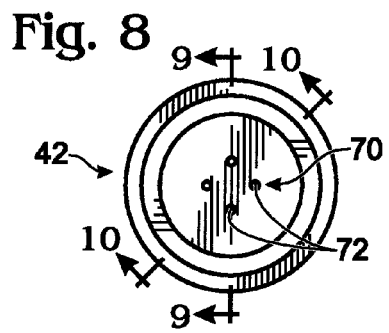
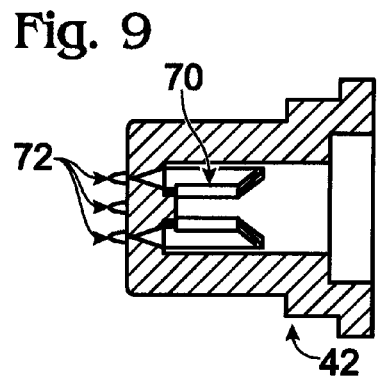
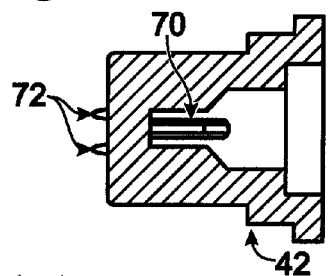
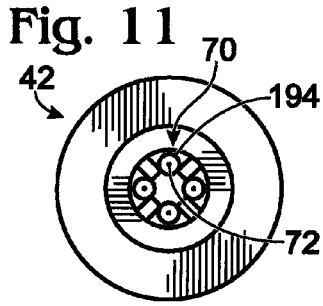
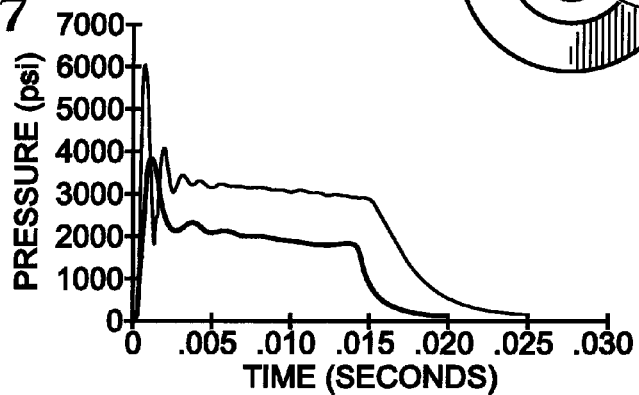
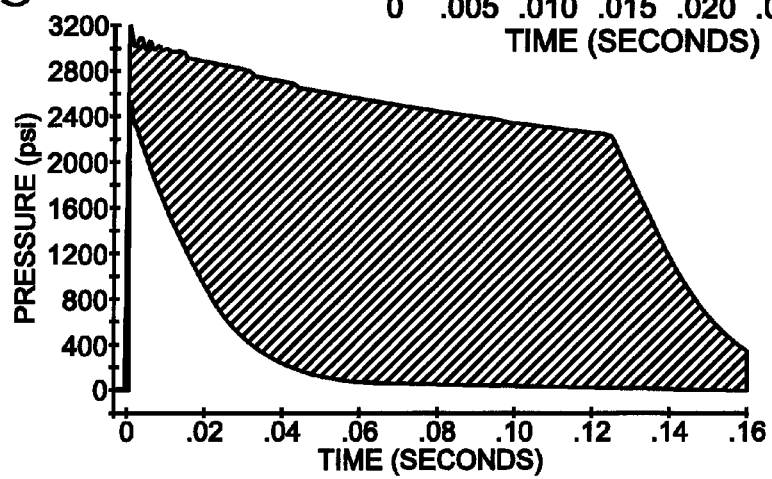

NEEDLE-FREE INJECTOR AND PROCESS FOR PROVIDING SERIAL INJECTIONS

CROSS-REFERENCE TO RELATED APPLICATIONS

This application claims priority under 35 U.S.C. 119(e) to U.S. Provisional Patent Application No. 60/826,204 entitled "NEEDLE-FREE INJECTOR FOR SERIAL INJECTIONS," filed Sep. 19, 2006, the disclosure of which is incorporated herein by reference.

BACKGROUND

Needle-free injection systems provide an alternative to standard injectate delivery systems, which generally use a needle adapted to penetrate the outer surface of a target. Typically, needle-free injection systems are designed to eject the injectate, such as a liquid drug, from a chamber with sufficient pressure to allow the injectate to penetrate the target to the desired degree. For example, common applications for needle-free injection systems include delivering intradermal, subcutaneous and intramuscular injections into or through a recipient's skin. For each of these applications, the injectate must be ejected from the system with sufficient pressure to allow the injectate to penetrate the tough exterior dermal layers of the recipient's skin.

Examples of needle-free injection systems and components are found in U.S. Pat. Nos. 4,596,556, 4,790,824, 4,940,460, 4,941,880, 5,064,413, 5,312,335, 5,312,577, 5,383,851, 5,399,163, 5,503,627, 5,505,697, 5,520,639, 5,746,714, 5,782,802, 5,893,397, 5,993,412, 6,096,002, 6,132,395, 6,216,493, 6,264,629, 6,319,224, 6,383,168, 6,415,631, 6,471,669, 6,572,581, 6,585,685, 6,607,510, 6,641,554, 6,645,170, 6,648,850, 6,623,446, 6,676,630, 6,689,093 6,709,427, 6,716,190, 6,752,780, 6,752,781, 6,783,509, 6,935,384, 6,942,645, 6,979,310, 6,981,961, 7,056,300 and 7,156,823; U.S. Patent Application Publication No. 2006/0189927; and International Publication No. WO 00/72908, the disclosures of which are incorporated herein by reference, in their entirety and for all purposes.

SUMMARY

The present disclosure is directed to needle-free injection devices having a delivery system to effect an injection from a body of the device. The delivery system includes an injectate assembly that houses a volume of liquid and a drive assembly that expels the liquid from the injectate assembly. The drive assembly may communicate with a compressed gas source. The delivery system may include a transmission assembly adapted to couple the drive assembly with the injectate assembly. The injection devices may include a dosing assembly to transfer injectate from an injectate source to the dosing assembly. The device may further include a nozzle assembly having one or more ports.

The advantages of the disclosed needle-free injection system may be understood more readily after a consideration of the drawings and the Detailed Description.

BRIEF DESCRIPTION OF THE DRAWINGS

FIG. 1 is a schematic diagram of an illustrative needle-free injection system configured to perform serial injections.

FIG. 2 is an exploded view of an exemplary needle-free injection system configured to perform serial injections.

FIG. 3 is a sectional side elevation view of the injection system of FIG. 2.

FIG. 4 is a sectional side elevation view of an exemplary injection system showing a transmission assembly including an impact gap.

FIG. 8 is a front view of an exemplary nozzle body suitable for use with the injection system of FIGS. 1-5 and having four ports.

FIG. 9 is a sectional side elevation view of the nozzle body of FIG. 8 along lines 9-9.

FIG. 10 is a sectional side elevation view of the nozzle body of FIG. 8 along lines 10-10.

FIG. 11 is a rear view of the nozzle body of FIG. 8 showing positioning of orifice inserts within the ports.

FIG. 17 illustrates exemplary pressure profiles of the injection systems of FIGS. 1-5.

FIG. 18 illustrates exemplary pressure ranges during delivery of various volumes of injectate using the devices of FIGS. 1-5.

DETAILED DESCRIPTION

Figure 5:
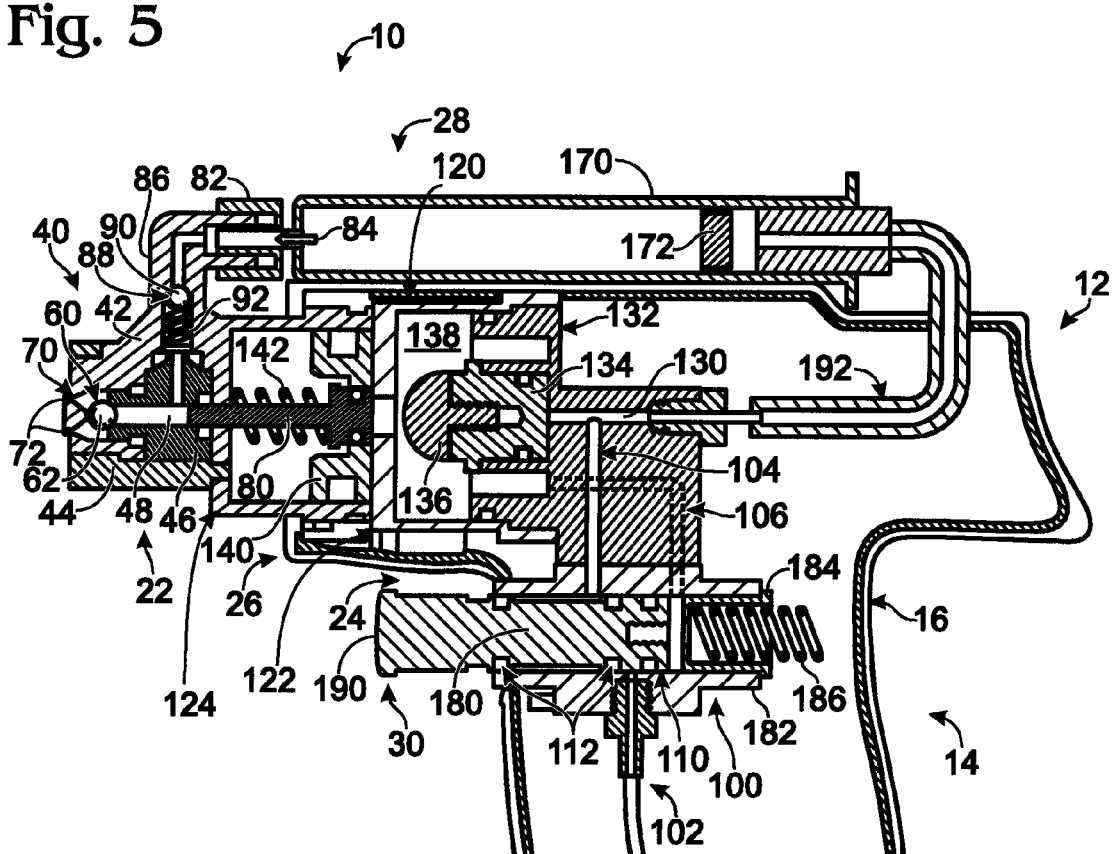
FIG. 5 is a sectional side elevation view of another exemplary needle-free injection system configured to perform serial injections.

FIGS. 1-9 illustrate needle-free injection systems and devices that deliver serial injections of an injectate. It should be appreciated that the various systems and/or components of the device may be configured for multiple or single use and for use with any suitable type of injectate. Suitable injectates include, but are not limited to, gel and other fluid formulations for use in cosmetic applications such as tissue augmentation, vaccines, drugs, and other injectable materials. Injectates for use in cosmetic applications include Botox and collagen formulations. Cosmetic injectates tend to be more viscous than drugs typically injected by needle-free devices and prior needle-free devices may therefore not be suitable for use with cosmetic injectates.

As illustrated in FIG. 1, devices 10 include one or more systems to effect an injection. For example, the devices may include a delivery system 12 and an actuation system 14. The delivery system provides an interface for delivery of an injectate to a recipient and expels a volume of injectate from the device. The actuation system actuates the delivery system to expel the injectate. Device 10 includes a body, or housing, 16 to contain or assist in coupling the various systems. The housing may include two or more portions that may be coupled together using any suitable method or mechanism, such as by screws. Any housing configuration and component materials may be used as are suitable for ease of assembly of the device, ergonomic factors, injectate interaction, and fabrication methods.

Delivery system 12 includes an injectate assembly 22 for housing an injectate and providing an interface with a recipient's skin. The delivery system also includes a drive assembly 24 to provide a driving or operative force to the injectate assembly to effect an injection. Consequently, the injectate assembly is adapted to eject a volume of injectate responsive to application of an operative force to the injectate assembly from the drive assembly. In some configurations of the device, a transmission assembly 26 may be provided to couple the injectate assembly and the drive assembly. Alternatively, the drive assembly may be coupled directly to the injectate assembly. In some configurations, the drive assembly may deliver, directly or indirectly via the transmission assembly, energy from an energy supply, such as a source of compressed gas, to an energy reserve, such as a storage reservoir. The transmission assembly may then deliver the operative force to the injectate assembly using the energy reserve.

In some versions of the device, a dosing assembly 28 may be included in the delivery system to assist a user in preparing an initial and/or specific dose to be injected and/or to automatically prepare the device for another injection. The dosing assembly is configured to transfer injectate from an injectate source to the injectate assembly and may therefore be biased to urge injectate towards the injectate assembly. For example, the dosing assembly may use a portion of the energy available to the drive assembly, such as excess energy like exhaust gas, to urge injectate from the injectate source into the injectate assembly. In such a configuration, the dosing assembly functions as a feed assist to urge injectate into the injectate assembly for the next injection. The device may be configured to use excess energy from other sources, such as in spring-powered devices or injection devices including electric motors.

Actuation system 14 includes a trigger assembly 30, which assists a user in selectively actuating the drive assembly, either directly or indirectly, to deliver an injection. The trigger assembly therefore may be configured to restrict selectively operation of the drive assembly. The trigger assembly may include any suitable safety mechanisms to restrict inadvertent actuation of the device or actuation prior to appropriate preparation of the device.

The exemplary device of FIG. 2 illustrates a housing 16 including a view port 18. The view port may enable a user to view interior components of the device, such as to determine the remaining amount of injectate. In some configurations, view ports may provide additional information to a user, such as related to availability of pressurized gas for further injections by a gas-powered device or other status indicators of the device.

FIGS. 2 and 3 illustrate a non-exclusive example of device 10 that includes an injectate assembly 22, a drive assembly 24, a transmission assembly 26, a dosing assembly 28, and a trigger assembly 30. As previously discussed with respect to FIG. 1, the device is configured to perform serial injections.

In the exemplary device of FIGS. 2 and 3, injectate assembly 22 includes a nozzle assembly 40 to house the injectate and provide an interface with a recipient's skin. The nozzle assembly includes a nozzle body 42, a nozzle retainer 44, and an injectate housing 46. The injectate housing forms an injectate chamber 48 for receiving and/or storing a dosage of injectate that is to be expelled through the nozzle assembly. In some versions of the device, chamber 48 may be configured for storage and/or mixing of lyophilized materials. The nozzle retainer couples the nozzle body to the device, such as to the injectate chamber.

Nozzle body 42 includes an injectate outlet valve 60 that restricts movement of materials, such as injectate, out of the nozzle assembly or external air from entering the nozzle assembly when a fresh dose of injectate is drawn into the nozzle. In the exemplary device of FIGS. 2 and 3, the injectate outlet valve includes a movable plug member 62, such as a nitrile ball, positioned within a receiving chamber 64. Injectate may pass around the plug member when the plug member is in an open position (leftward with respect to FIG. 3). When the plug member is in the closed position (rightward as shown in FIG. 3), it presses against outlet valve seat 66, to prevent movement of injectate through the valve. The plug member may be biased, such as by a spring, to one of the open or closed positions. As described in U.S. Pat. No. 6,264,629, the disclosure of which is incorporated in its entirety, the interior of the nozzle body may include one or more channels through which fluid may bypass the plug member to provide an open flow path with outlet orifices in the nozzle. Alternatively, or additionally, the plug member may include ribs or slots, such as described in U.S. Pat. No. 6,132,395, to provide bypass channels for fluid communication with outlet orifices in the nozzle body. The plug member may also be deformable when subjected to operating pressures, allowing fluid to flow around the plug, but disallow air intrusion at atmospheric pressure while injectate is being drawn into the nozzle.

Nozzle body 42 includes one or more ports 70, each port terminating in an outlet orifice 72. The orifice(s) may be integrally formed with the port(s) or may be formed by the placement of a separate component within the respective port, as will subsequently be discussed. In the example shown in FIGS. 2 and 3, a plunger 80 is slidably disposed within injectate chamber 48, thereby defining a variable-volume fluid reservoir between the plunger and injectate outlet valve 60. When plunger 80 is advanced (i.e., moved to the left in FIG. 3), the injectate is expelled out of the chamber and through the outlet valve and outlet orifices 72. Retraction of plunger 80 (i.e., moving the plunger to the right in FIG. 3) draws injectate into chamber 48 via dosing assembly 28. The outlet plug member is held against valve seat 66 as the plunger is retracted to prevent fluid or contaminants from being drawn into injectate chamber 48 through the outlet orifice. A spring or other biasing structure (not shown) may be provided to urge the outlet plug member to the closed position. As plunger 80 advances, outlet plug member 62 moves away from engagement with seat 66 or deforms, allowing fluid to pass around the plug member and out of the nozzle body through outlet 72.

The nozzle assembly may include any suitable sealing mechanisms. For example, an O-ring may be used to provide a seal between the nozzle body and the nozzle retainer. It should be appreciated that nozzle assembly 40 is presented as an illustrative example and that other variable-volume components may be employed. For example, a squeezable bulb or elastomeric bladder may be used to expel fluid from the device.

Dosing assembly 28 prepares a dose, such as of a predetermined quantity, to be injected. The dosing assembly couples an injectate source (not shown) with nozzle assembly 40. In the exemplary configuration of FIGS. 2 and 3, the dosing assembly includes an adapter 82 to couple the dosing assembly to the injectate source so that injectate enters along flow path 84. Adapter 82 may take the form of a banjo adapter that provides a luer fitting for a vial, syringe, or other injectate source, through which the injectate may be moved to prepare the device for an injection. However, any suitable adapter or fitting may be used to couple the injectate source with the device.

In the exemplary configuration of FIGS. 2 and 3, the dosing assembly includes a dose housing 86 having an injectate inlet valve 88 to draw in or otherwise allow injectate to enter chamber 48 while preventing backflow of injectate towards the injectate source. Any suitable valve may be used, including but not limited to, a ball-type check valve, and may be configured similarly to injectate outlet valve 60. For example, the injectate inlet valve may include a movable inlet plug member 90, such as a nitrile or stainless steel check ball, disposed within a refill chamber 92. The plug member may be urged upward into a closed position against an inlet valve seat of refill chamber 92, as shown in FIG. 3, during an injection. As plunger 80 retracts, the inlet valve is opened as inlet plug member 90 is pulled downward, as shown in FIG. 3, in response to the resulting vacuum and allows injectate to be drawn into refill chamber 92. Consequently, movement of the inlet plug member and plunger draws in more injectate to prepare the device for a subsequent injection.

The injectate assembly and/or dosing assembly may be adjustable to allow variation of the maximum amount of injectate that may be drawn into and/or expelled from chamber 48. Specifically, the outer circumference of injectate housing 46 may include threads 94 that engage with adjacent components, such as transmission assembly 26, to vary the plunger's permitted range of motion by adjusting the maximum amount by which plunger 80 may be withdrawn through chamber 48. This adjusts the maximum volume of chamber 48. Various locking mechanisms may be used to maintain a desired chamber volume.

The injectate source may be mounted to the dosing assembly and remain mounted to the dosing assembly during an injection sequence. Consequently, serial injections may be performed more quickly than if a user had to connect and remove a filling adapter between each injection to refill the device.

The drive assembly 24 provides a driving force to effect an injection. In some configurations, the drive assembly delivers energy from an energy supply (not shown) to an energy reserve. For example, the drive assembly may include a gas supply system to provide an operative force for delivering an injection. The device may include a storage reservoir to replenish the gas supply between serial injections. Consequently, the device is more quickly prepared for a subsequent injection. The gas system may use gas supplied directly from the pressurized gas source, such as an external tank or cartridge. In some configurations, gas may be provided through pyrotechnics. In still other configurations, the drive assembly may be powered by one or more springs or one or more electric motors.

In the exemplary device of FIGS. 2 and 3, the drive assembly includes a supply valve assembly 100 configured to control the supply of compressed gas that is used to deliver an operative force to plunger 80. One or more suitable coupling members 102, such as fittings and/or feed lines, may be provided to supply the injection device with an energy source, such as a compressed gas tank via a gas hose (not shown). The delivery of pressurized gas through the device typically is controlled by the supply valve assembly, which is actuated via operation of trigger assembly 30. The supply valve assembly may include one or more valves that are biased to a closed position, such as by springs, until actuated by trigger assembly 30 to an open position.

The exemplary supply valve assembly includes one or more valves that regulate the effects of gas flow on the injectate assembly, such as by regulating gas flow from an energy supply to an energy reserve, such as via the transmission assembly. In the illustrative example of FIG. 3, supply valve assembly 100 regulates gas flow along a sealing path 104, which seals a portion of the transmission assembly such as to seal an energy reserve, and along a drive path 106, which provides gas to the sealed portion such as to fill the energy reserve, for subsequent delivery of an injection. The valves of the supply valve assembly may be independently actuated to control gas flow along the sealing path and the drive path.

In the exemplary device of FIGS. 2 and 3, the supply valve assembly includes a sealing valve 110 and a drive valve 112 that regulate gas flow to the sealing path 104 and drive path 106, respectively. The sealing and drive valves may take the form of three-way valves. In the depicted example, trigger assembly 30 may first actuate the sealing valve to allow gas to flow along the sealing path to seal a portion of the transmission assembly. The trigger assembly then actuates the drive valve to allow gas to flow along the drive path to fill the sealed portion of the transmission assembly with a suitable amount of compressed gas to deliver an injection. The sealing and drive valves may be supported relative to the trigger assembly using any suitable component, such as a valve bracket 114. In the example shown, the valves are actuated by the trigger assembly pressing against valve stems 116, 118. The valves may be connected to one or more pressurized gas sources, such as gas tanks, using one or more coupling members 102.

Transmission assembly 26 delivers an operative force to the injectate assembly using the energy reserve of the drive assembly. For example, the transmission assembly may transfer compressed gas from the drive assembly to the injectate assembly, such as to move plunger 80. In the exemplary device of FIGS. 2 and 3, the transmission assembly includes a reservoir seal valve 120, a storage reservoir housing 122, and a transfer chamber 124. Gas is directed along drive path 106 through the seal valve into the storage reservoir housing and then is released into the transfer chamber to deliver an injection.

In the illustrative example of FIGS. 2 and 3, the reservoir seal valve includes a reciprocating valve structure, such as a pneumatically driven poppet valve. Additional examples of a suitable seal valve are described in U.S. Pat. No. 7,156,823, the disclosure of which is incorporated in its entirety. Pressurized gas enters along sealing path 104 into a poppet reservoir 130, formed by valve housing 132, to move the reservoir seal valve to a closed position, such as by urging poppet 134 to the left as shown in FIG. 3. The poppet thereby presses a poppet seal 136 against an opening in a bulkhead of a storage reservoir housing 122 to seal off the housing and form an energy reserve, such as a gas storage reservoir 138.

Pressurized gas enters the storage reservoir through drive path 106 to fill the storage reservoir once the opening is sealed by the poppet seal. Forward and aft movement of the poppet is determined by the relative gas pressures in the poppet reservoir and the gas storage reservoir. Once the storage reservoir is sufficiently filled by compressed gas, the poppet seal is urged away from the storage reservoir opening and the compressed gas is released into the transfer chamber to drive plunger 80 and/or a gas piston 140 to the left as shown in FIG. 3 to deliver an injection. The piston and/or plunger may be biased, such as by a return spring 142, to return to a position against the bulkhead, such as during venting of pressurized gas remaining once the injection is completed.

The plunger and piston may be movable relative to one another, coupled to one another such as by a seal, or integrally formed with one another. The piston may be configured to move in tandem with the plunger, such as when the piston and plunger are integrally formed, coupled by a seal, or the piston and plunger may be configured to allow relative movement therebetween. In the example depicted in FIG. 2, gas piston 140 is adjacent the bulkhead opening and urges the plunger leftward to deliver an injection in response to compressed gas entering the transfer chamber. In the example shown in FIG. 4, plunger 80 is adjacent the bulkhead opening and biased to a closed position by spring 142. The plunger includes a lip 150 that extends beyond the central opening of piston 140. As the reservoir seal valve is opened and gas flows towards transfer chamber 124, piston 140 is urged leftward until it impacts lip 150. The gas pressure against the piston and plunger overcomes the bias provided by spring 142 to deliver an injection. Movement of the piston thereby creates an impact gap. The momentum of the piston impacting the catchment lip of the plunger creates a spike in the pressure profile of the injectate, and results in shorter rise times and higher peak pressures than when the impact gap is not utilized.

Exhaust gas not used to deliver an injection may be routed towards the injectate source to urge injectate along flow path 84. Any suitable valves, fittings, and the like may be used to provide such a feed assist for the device of FIGS. 2 and 3. In devices having other sources of power, such as spring-powered devices, other suitable components may be used to route excess energy to the injectate source to provide an injectate feed assist. For example, in a spring-powered device, spring recoil or unused spring force may be used to urge injectate into the dosing assembly to assist in preparing the device for a subsequent injection. Alternatively, or additionally, the device may use the exhaust gas, or a portion thereof, to assist in marking the location of the injection. For example, the device may include a dye marker, such as disclosed in U.S. Pat. No. 7,156,823, to mark the location of the injection.

In the exemplary device of FIGS. 2 and 3, trigger assembly 30 includes a trigger button 152 to selectively actuate the supply valve assembly. When pressed, the button rotates a trigger lever 154 to actuate supply valve assembly 100 by pressing against valve stems 116, 118. The trigger lever pivots in an arcuate slot 156 of an extension of the valve bracket. The valve stem of the sealing valve is opened to allow gas to drive the poppet forward. As the button is depressed further, the trigger lever impinges upon the stem of the drive valve to open the drive valve and fill the gas reservoir. As the fulcrum of the trigger lever is moved to the drive valve stem, the sealing valve stem is released and the valve closes. Gas pressure is thus released from behind the poppet back into the corresponding valve, thereby triggering the device. A spring 158 adjacent the valve bracket biases the lever to the left of the slot, as shown in FIG. 3, and is tuned to ensure both supply valves are open for a sufficient time to fill the gas reservoir. Consequently, the trigger assembly is adapted to actuate the valves independently of one another.

FIG. 5 illustrates another exemplary device 10 configured to provide for serial injections. As shown, delivery system 12 includes an injectate assembly 22 for housing an injectate and providing an interface with a recipient's skin, and a drive assembly 24 to provide a driving or operative force to the injectate assembly to effect an injection. Transmission assembly 26 couples the injectate assembly and the drive assembly. Dosing assembly 28 assists a user in preparing an initial and/or specific dose to be injected and/or to automatically prepare the device for another injection. The dosing assembly may urge injectate into the injectate assembly for the next injection. The device further has an actuation system 14 that includes a trigger assembly 30, which assists a user in selectively actuating the drive assembly.

In the exemplary device of FIG. 5, the nozzle assembly includes a nozzle body 42, a nozzle retainer 44, and an injectate housing 46, similar to that discussed above. The injectate housing forms an injectate chamber 48 for a dosage of injectate that is to be expelled through the nozzle.

Nozzle body 42 includes an injectate outlet valve 60 that restricts movement of materials, such as injectate, through the end of the nozzle body. In the exemplary device of FIG. 5, the injectate outlet valve includes a movable plug member 62 positioned within a receiving chamber similar to that previously described. Injectate may pass around the plug member when the plug member is in an open position (leftward with respect to FIG. 5) or deformed under high pressure. When the plug member is in the closed position (rightward as shown in FIG. 5), it presses against an outlet valve seat, to prevent movement of injectate or air through the valve.

Nozzle body 42 includes one or more ports 70, each port terminating in an outlet orifice 72. The orifice(s) may be integrally formed with the port(s) or may be formed by the placement of a separate component within the respective port, as will subsequently be discussed. In the example shown in FIG. 5, a plunger 80 is slidably disposed within injectate chamber 48, thereby defining a variable-volume fluid reservoir between the plunger and injectate outlet valve 60. When plunger 80 is advanced, the injectate is expelled out of the chamber and through the outlet valve and outlet orifice(s) 72. Retraction of plunger 80 draws injectate into chamber 48 via dosing assembly 28. The outlet plug member is held against the valve seat as the plunger is retracted to prevent fluid or contaminants from being drawn into chamber 48 through the outlet orifice. As plunger 80 advances, outlet plug member 62 moves away or deforms away from engagement with the valve seat, allowing fluid to pass around the plug member and out of the nozzle body through outlet 72.

The dosing assembly couples an injectate source 170, such as a syringe, with nozzle assembly 40. In the exemplary configuration of FIG. 5, the dosing assembly includes an adapter 82 to couple the dosing assembly to the injectate source so that injectate enters along flow path 84. Adapter 82 may take any suitable form that couples injectate source 170 with nozzle assembly 40, such as nozzle 42 or injectate housing 46. Movable within the syringe is a source plunger 172. The injectate source may include a choke valve (not shown) or other suitable structure to prevent backflow of the injectate.

In the exemplary configuration of FIG. 5, the dosing assembly includes a dose housing 86 having an injectate inlet valve 88 to draw in or otherwise allow injectate to enter chamber 48 while preventing backflow of injectate towards the injectate source. In some configurations of the device, such as shown in FIG. 5, the dose housing may be integrally formed with nozzle body 42.

Any suitable valve may be used, including but not limited to, a ball-type check valve, similar to that previously discussed. For example, the injectate inlet valve may include a movable inlet plug member 90, such as a nitrile or stainless steel check ball, disposed within a refill chamber 92. The plug member may be urged upward into a closed position against an inlet valve seat of chamber 92, as shown in FIG. 5, during an injection. As plunger 80 retracts, the inlet valve is opened as inlet plug member 90 is pulled, downward as shown in FIG. 5, in response to the resulting vacuum and allows injectate to be drawn into chamber 92. Consequently, movement of the inlet plug member and plunger draws in more injectate to prepare the device for serial injections.

In the exemplary device of FIG. 5, the drive assembly includes a supply valve assembly 100 configured to control the supply of compressed gas that is used to deliver an operative force to plunger 80. One or more suitable coupling members 102, such as fittings and/or feed lines, may be provided to pass through housing 16 to supply the injection device with an energy source, such as a compressed gas tank via a gas hose (not shown). The delivery of pressurized gas through the device typically is controlled by the supply valve assembly, which is actuated via operation of trigger assembly 30. The supply valve assembly may include one or more valves that are biased to a closed position, such as by springs, until actuated by trigger assembly 30 to an open position.

The exemplary supply valve assembly includes one or more valves that regulate the effects of gas flow on the injectate assembly, such as by regulating gas flow to the transmission assembly. In the illustrative example of FIG. 5, supply valve assembly 100 regulates gas flow along sealing path 104, which seals a portion of the transmission assembly, and along drive path 106 (shown in dashed lines behind the sealing path), which provides gas to the sealed portion for subsequent delivery of an injection.

In the exemplary device of FIG. 5, the supply valve assembly includes a slide valve having a series of bores or channels around a valve core 180 that operate as the sealing valve 110 and the drive valve 112 to regulate gas flow to the sealing path 104 and drive path 106, respectively. The sealing and drive valves may be integrally formed in the valve core so that when the trigger assembly 30 is actuated the sealing valve is opened to allow gas to flow along the sealing path to seal a portion of the transmission assembly, and then the drive valve is opened to allow gas to flow along the drive path to fill the sealed portion of the transmission assembly with a suitable amount of compressed gas to deliver an injection. Therefore, as the valve core slides, it aligns one or more channels to selectively open the sealing and drive paths. The valve core is movable within a valve housing 182 and restricted by a valve cup 184. The valve cup may be biased, such as by spring 186, to return the supply valve assembly to its initial position and close the sealing and/or drive valves. The supply valve assembly may be connected to one or more pressurized gas sources, such as gas tanks, using one or more coupling members 102.

Similar to that of the device of FIGS. 2 and 3, transmission assembly 26 of the exemplary device of FIG. 5 includes a reservoir seal valve 120, a storage reservoir housing 122, and a transfer chamber 124. Compressed gas is directed along drive path 106 through the seal valve into the storage reservoir housing and then is released into the transfer chamber to deliver an injection.

The reservoir seal valve includes a reciprocating valve structure, such as a pneumatically driven poppet valve. Pressurized gas enters along sealing path 104 into a poppet reservoir 130, formed by valve housing 132, to move the reservoir seal valve to a closed position, such as by urging poppet 134 to the left as shown in FIG. 5. The poppet thereby presses a poppet seal 136 against an opening in a bulkhead of storage reservoir housing 122 to seal off the housing and form a storage reservoir 138.

Pressurized gas enters the storage reservoir through drive path 106 to fill the storage reservoir once the opening is sealed by the poppet seal. Forward and aft movement of the poppet is determined by the relative gas pressures in the poppet reservoir and the gas storage reservoir. Once the storage reservoir is sufficiently filled by compressed gas, the poppet seal is urged away from the storage reservoir opening and the compressed gas is released into the transfer chamber to drive plunger 80 and/or a gas piston 140 to the left as shown in FIG. 5 to deliver an injection. The piston and/or plunger may be biased, such as by a return spring 142, to return to a position against the bulkhead, such as during venting of pressurized gas remaining once the injection is completed.

The plunger and piston may be movable relative to one another, coupled to one another such as by a seal, or integrally formed with one another. The piston may be configured to move in tandem with the plunger, such as when the piston and plunger are integrally formed, coupled by a seal, or the piston and plunger may be configured to allow relative movement therebetween. In the example depicted in FIG. 5, the plunger includes a catchment lip, as discussed with respect to FIG. 4, to create a faster rise in the pressure profile of the injectate.

The trigger assembly of the exemplary device of FIG. 5 includes a trigger 190 to actuate the drive assembly. Trigger 190 may be integrally formed with valve core 180 so that actuation of the trigger, such as by a user pressing the trigger rightward against the valve spring as shown in FIG. 5, opens sealing valve 110 and drive valve 112 in the desired order and timeframe to fill gas storage reservoir 138. As the valve core moves through the valve housing, the bores, or channels, in the valve core align with channels in the valve housing that lead into sealing path 104 and drive path 106 to perform an injection.

Exhaust gas not used to deliver an injection may be routed towards the injectate source to urge injectate along flow path 84. Any suitable valves, fittings, and the like may be used to provide such a feed assist. In the exemplary device of FIG. 5, exhaust gas flows along feed assist path 192 to the rear of the injectate source 170 to apply pressure to source plunger 172 to urge the injectate through adapter 82 and prepare the device for a subsequent injection.

Figure 6:
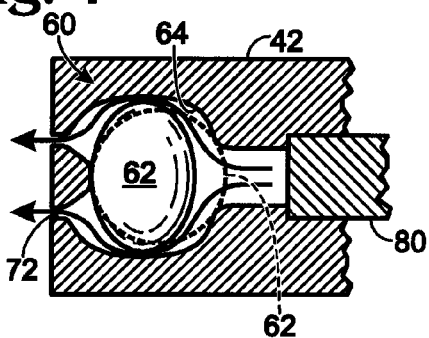
FIG. 6 is a sectional side elevation view of an exemplary nozzle body with an outlet valve suitable for use with the injection system of FIGS. 1-5

As previously discussed, nozzle body 42 may include an injectate outlet valve 60 that restricts movement of materials, such as injectate, out of the nozzle assembly or external air from entering the nozzle assembly when a fresh dose of injectate is drawn into the nozzle. In the exemplary outlet valve of FIG. 6, a movable and deformable plug member 62, such as a nitrile ball, is positioned within a receiving chamber 64. When the plug member is in the closed position (rightward in dashed lines as shown in FIG. 6), it presses against an outlet valve seat, to prevent movement of injectate through the valve. Injectate may pass around the plug member when the plug member is in an open position (leftward and deformed as shown in solid lines in FIG. 6). The interior of the nozzle body may include one or more ribs 68 that form channels therebetween through which fluid may bypass the plug member to provide an open flow path to the outlet orifices in the nozzle. In the example shown in FIG. 6, the plug member is deformable when subjected to operating pressures, allowing fluid to flow around the plug and through the channels between the ribs out of orifice 72, but restricting air intrusion at atmospheric pressure while injectate is being drawn into the nozzle.

Figure 7:
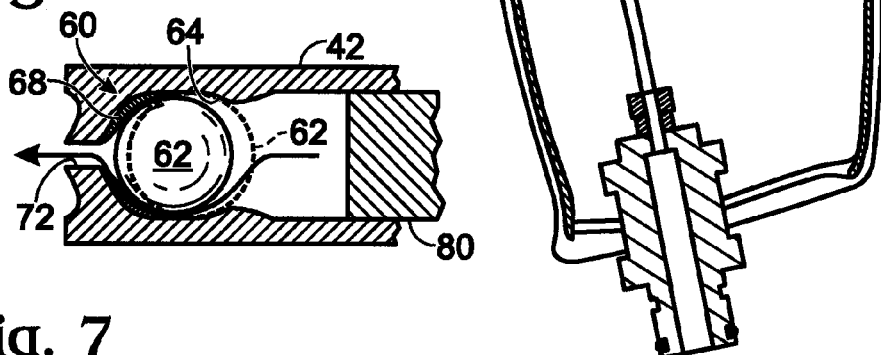
FIG. 7 is a sectional side elevation view of another exemplary nozzle body with an outlet valve suitable for use with the injection system of FIGS. 1-5

FIG. 7 illustrates another exemplary nozzle body 42 that includes an injectate outlet valve 60 that restricts movement of materials through the nozzle assembly. In the exemplary outlet valve of FIG. 7, a movable and deformable plug member 62 is positioned within receiving chamber 64. When the plug member is in the closed position (rightward in dashed lines), it presses against an outlet valve seat to prevent movement of injectate through the valve. Injectate may pass around the plug member when the plug member is in an open position (leftward and deformed as shown in solid lines). The outlet valve may control flow through a plurality of orifices 72.

The nozzle body may have any suitable number of ports, including, but not limited to one, two, three, four, five, etc. The exemplary device of FIGS. 2-3, 5 and 8-11 illustrates a nozzle body having four ports, the exemplary device of FIG. 4 illustrates a nozzle body having a single port, and the device of FIG. 5 illustrates a nozzle body having two ports. Similarly to a single orifice nozzle body, a multi-orifice nozzle body produces a well developed and concentrated flow starting at the beginning of the injection and remaining columnated during an injection. FIGS. 8-10 illustrate front and cross-sectional views of an exemplary nozzle body including four ports that may be used with the device of FIGS. 1-5. The ports and/or orifices may be parallel, may diverge, or may form any other configuration suitable for delivering an injection.

FIG. 11 illustrates a rear view of the exemplary nozzle body of FIG. 8. As shown, four ports are used in a symmetric pattern to distribute an injection over a greater surface area than a single port. Within each port may be an insert 194 to form the orifice, such as integrally formed inserts like a ruby or sapphire jewel orifice manufactured by Bird Precision. These jewel inserts are configured to form precision orifices. For example, approximately 0.003-0.005 inch (approximately 0.07-0.13 millimeters) diameter ruby orifices have been found to produce desirable results. In the quad-port example shown, such inserts would produce a total orifice cross-sectional area of approximately 0.00028-0.00079 square inches (0.015-0.05 square millimeters). The inserts may be positioned at a distal end of each port.

Figure 12:
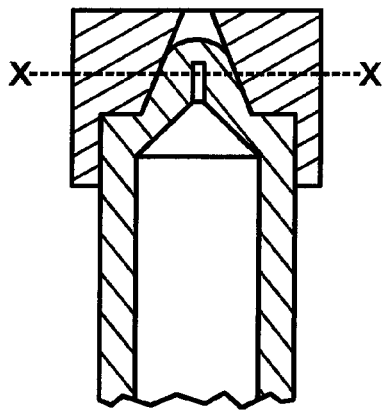
FIG. 12 is a sectional side elevation view of a prior nozzle body forming method.

As illustrated in FIG. 12, nozzle orifices have previously been formed by placing a mandrel with a pin inside a nozzle body and pressing a forming tool against the opposite side of the nozzle body to conform the material to the shape of the mandrel. The nozzle body is then cut alone line X-X to remove the end nub and provide a nozzle orifice. The orifice edges are further processed to produce a smooth surface. One complication with such a forming process is that the pin may break. Since the pin is housed within a molding tool, the failure of the pin may not be noticed until a series of nozzle bodies are inspected. Further, removal of the end nub may irreparably damage the orifices. For example, in plastic nozzle bodies, removal of nubs may smear plastic across the orifice, particularly as this procedure is repeated for each orifice.

Each port and/or orifice may be integrally formed through the nozzle body using various methods of plastic injection molding, machining, laser drilling, and the like as is suitable for the material of the nozzle body and the desired size of the ports and/or orifices. The ports and orifices may have the same diameter or differing diameters, such as when the ports provide a stepped-down bore leading to a smaller diameter orifice.

Figure 13:
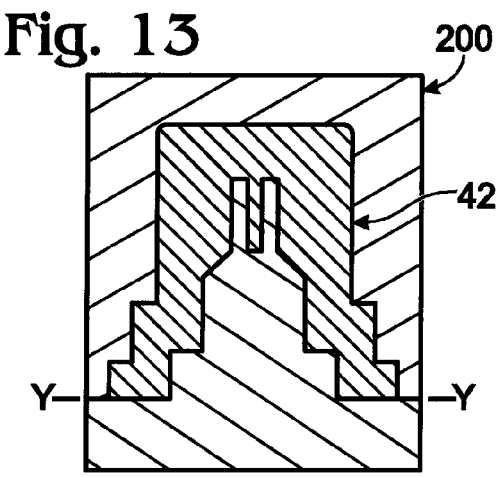
FIG. 13 is a sectional side elevation view of an exemplary forming method of a nozzle body having two ports.
Figure 14:
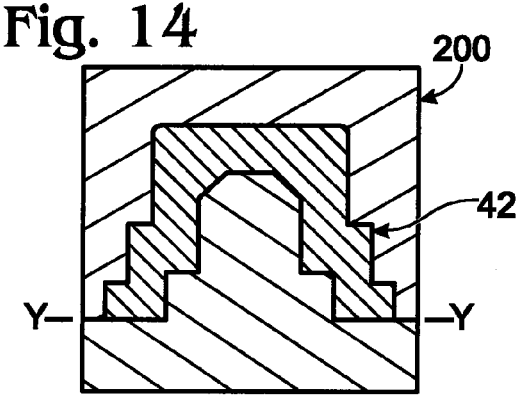
FIG. 14 is a sectional side elevation view of an exemplary forming method of a nozzle body.
Figure 15:
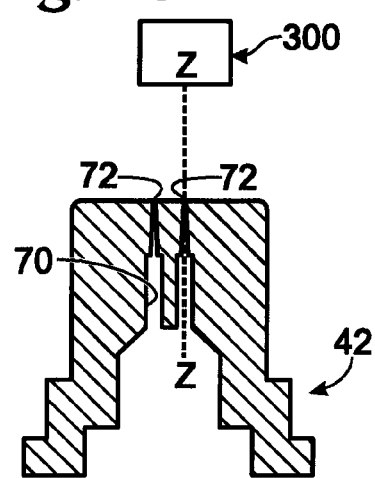
FIG. 15 is a sectional side elevation view of a laser drilling method of forming an orifice corresponding to each port of the nozzle body of FIG. 13.
Figure 16:
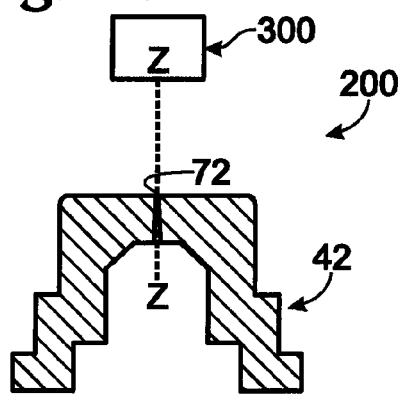
FIG. 16 is a sectional side elevation view of a laser drilling method of forming an integral port and orifice in the nozzle body of FIG. 14.

Since plastic injection molding is a two step process that results in delicate ports and orifices that will be subjected to high pressures, laser drilling may be used to form the ports and/or orifices. For example, the nozzle body may be formed using various plastic molding methods, whereas the ports and/or orifices may be formed using laser drilling. In some embodiments, the ports may be formed through a molding process, as shown in FIGS. 13 and 14, in which a forming mold 200 is pressed together along Y-Y. As shown in FIGS. 15 and 16, a laser source 300 may then be directed towards the ports from either end of the nozzle body along axis Z-Z to form or adjust the orifices.

Laser drilling may be done on an as-needed basis from a single set of blank nozzle bodies, thus reducing the need for storage of pre-formed components. Therefore, nozzle bodies having different orifice configurations may be produced from a single set of molded nozzle bodies. Laser drilling also produces orifices having smooth distal ends, therefore negating the extra step of removing a distal nub created during prior forming processes, such as shown in FIG. 12 or plastic injection molding in which a metal fiber is pulled through the nozzle body to create each orifice. Any suitable laser source may be used, including, but not limited to, an excimer laser which produces light, typically in the ultraviolet range, that can remove exceptionally fine layers of surface material with almost no heating or change to the remainder of the material which is left intact. Moreover, the use of laser drilling also provides a confirmation process since the orifice diameter and configuration may be verified with the laser.

The disclosed devices may be configured to deposit injectate at various tissue depths depending on the application. For example, in cosmetic applications, the injectate may be deposited intradermally, rather than subcutaneously or intramuscularly. Depending on the orifice configuration and pressure profile, the device may include a spacer, such as described in U.S. Pat. No. 6,319,224, the disclosure of which is incorporated herein by reference, to provide an intradermal injection. However, the discussed devices having multiple orifices have been shown to not require a spacer to perform an intradermal injection. In particular, laser drilled orifices have a different shape than orifices formed through injection molding in that sharper contour transitions are produced with laser drilling. Laser drilled orifices are therefore less efficient (i.e., less fluid dynamic) than molded orifices, and thereby maintain a shallow injection depth, such as in the intradermal tissue. Further, the injection depth may be controlled by limiting the dose expelled through each orifice. A total delivered dose may be maintained based on the number of orifices used and/or the delivery pressure and duration, while using the diameter size to control the depth of penetration.

FIGS. 17 and 18 illustrate exemplary pressure profiles for the devices of FIGS. 1-5. The pressure profiles include an initial, or transient, peak pressure that is reached in a short period of time, known as the rise time. In the example shown, a peak pressure between 2500 and 6000 psi is reached within two milliseconds. This high initial pressure enables the liquid being injected to pierce the skin of the recipient. The pressure is then reduced to a damped peak pressure while the injection progresses, such as between 1800 and 3500 as shown in FIG. 17. As the injection is completed, as shown at approximately fifteen milliseconds, the pressure drops to a nominal value and the device is prepared for the next injection. It should be appreciated that the pressure profile may be adjusted based on the injectate viscosity and the desired depth of penetration.

FIG. 18 further illustrates exemplary pressure ranges during delivery of various volumes of injectate using the devices of FIGS. 1-5. The graph illustrates the possible delivery pressures of an injectate volume between 0.025 and 0.20 milliliters. As shown, larger volumes (the upper or right most limit) more easily reach a nominal peak pressure and maintain a desired delivery pressure. Consequently, minimum injectate volumes are typically above 0.05 milliliters.

Although the present invention has been shown and described with reference to the foregoing operational principles and preferred embodiments, it will be apparent to those skilled in the art that various changes in form and detail can be made without departing from the spirit and scope of the invention. The present invention is intended to embrace all such alternatives, modifications and variances. The subject matter of the present invention includes all novel and non-obvious combinations and subcombinations of the various elements, features, functions and/or properties disclosed herein. Inventions embodied in various combinations and subcombinations of features, functions, elements, and/or properties may be claimed through presentation of claims in a subsequent application.

What is claimed is:

1. A needle-free injection device for delivering serial injections comprising:

a body configured to house a plurality of systems;

a delivery system adapted to deliver an injection, the delivery system comprising:
- an injectate assembly adapted to eject a volume of injectate responsive to application of an operative force to the injectate assembly, the injectate assembly having a nozzle assembly including a chamber and one or more ports, each terminating in an outlet orifice, the nozzle assembly further including a plunger selectively movable within the chamber;
- a drive assembly adapted to provide the operative force to move the plunger using energy from an energy supply; and
- a dosing assembly configured to transfer injectate from an injectate source to the injectate assembly, wherein a portion of energy available to the drive assembly urges injectate from the injectate source to the injectate assembly; and an actuation system adapted to actuate the delivery system for delivery of an injection, the actuation system comprising:
- a trigger assembly configured to restrict selectively operation of the drive assembly.

2. The device of claim 1, wherein the energy supply is a compressed gas source, the drive assembly includes a supply valve assembly having one or more valves configured to control gas flow from the energy supply to an energy reserve, and the trigger assembly is adapted to actuate selectively the supply valve assembly.

3. The device of claim 2, wherein the supply valve assembly includes at least two valves and the trigger assembly is adapted to actuate the valves independently of one another.

4. The device of claim 2, wherein the supply valve assembly is configured to control gas flow along a sealing path that is configured to seal the energy reserve and a drive path that is configured to fill the energy reserve.

5. The device of claim 4, wherein a portion of the supply valve assembly is configured to slide and thereby align one or more channels to selectively open the sealing and drive paths.

6. The device of claim 4, wherein the supply valve assembly includes at least two valves that are independently actuated to control gas flow along the sealing path and the drive path.

7. The device of claim 1, wherein the injectate source is mounted to the dosing assembly and remains mounted to the dosing assembly during an injection sequence.

8. A delivery system for a needle-free injection device comprising:
- an injectate assembly adapted to eject a volume of injectate responsive to application of an operative force to the injectate assembly;
- a drive assembly adapted to provide the operative force to the injectate assembly using compressed gas, the drive assembly including a supply valve assembly configured to receive the compressed gas from a gas source and direct the compressed gas along a sealing path configured to seal a storage reservoir and a drive path configured to fill the storage reservoir; and
- a dosing assembly configured to fluidly couple an injectate source with the injectate assembly, wherein a portion of the gas received by the supply valve assembly urges injectate from the injectate source into the dosing assembly.

9. The delivery system of claim 8, wherein excess gas in the sealing path is directed along a feed assist path to urge injectate from the injectate source into the dosing assembly.

10. The delivery system of claim 8, wherein a portion of the supply valve assembly is configured to slide to selectively open the sealing path and the drive path.

* * * * *